United States Patent [19]
Melloni et al.

[11] Patent Number: 5,478,817
[45] Date of Patent: Dec. 26, 1995

[54] DIGITOXIGENIN AND DIHYDRODIGITOXIGENIN 3β-DERIVATIVES AND PHARMACEUTICAL COMPOSITIONS COMPRISING SAME FOR THE TREATMENT OF CARDIOVASCULAR DISORDERS

[75] Inventors: Piero Melloni, Bresso; Luigi Bernardi, Milan; Patrizia Ferrari, Varese; Mauro Gobbini, Mercallo; Marco Torri, Rho; Loredana Valentino, Buccinasco, all of Italy

[73] Assignee: Sigma-Tau Industrie Farmaceutiche Riunite S.p.A., Rome, Italy

[21] Appl. No.: 79,942

[22] Filed: Jun. 23, 1993

[30]     Foreign Application Priority Data

Jul. 1, 1992 [DE]   Germany .......................... 42 21 635.4

[51] Int. Cl.$^6$ .................. C07J 19/00; C07D 307/58; A61K 31/585
[52] U.S. Cl. .................. 514/175; 540/102; 540/104
[58] Field of Search .................. 540/102, 104; 514/175

[56]            References Cited

U.S. PATENT DOCUMENTS 4,259,240   3/1981   Werner et al. .................. 260/239.8 R

FOREIGN PATENT DOCUMENTS 2004543   8/1971   Germany .

OTHER PUBLICATIONS

Stoll et al, Helv. Chim. Acta vol. 17 pp. 592–613 (1934).
Jorgensen, Biochimica and Biophysica Acta vol. 356 pp. 36–52 (1974).
Erdmann et al, Arzneim Forsh vol. 34 pp. 1314–1318 (1984).
Mall et al, Biochem. Pharm. vol. 33 pp. 47–52 (1984).
Bobbio J. Org. Chem vol. 26 pp. 3023–3024 (1961).
Abramson et al, J. Pharm. Sciences vol. 66 pp. 602–603 (1977).
Weiss et al, Helvetica Chim Acta vol. 55 pp. 2452–2460 (1972).
Roder et al, J. Arch. Pharm vol. 318 pp. 837–842 (1985).

*Primary Examiner*—Nicholas Rizzo
*Attorney, Agent, or Firm*—Oblon, Spivak, McClelland, Maier & Neustadt

[57]            ABSTRACT

Digitoxigenin and dihydrodigitoxigenin 3β-derivatives, a process for their preparation and pharmaceutical compositions containing same for the treatment of cardiovascular disorders such as heart failure and hypertension are disclosed.

9 Claims, No Drawings

DIGITOXIGENIN AND DIHYDRODIGITOXIGENIN 3β-DERIVATIVES AND PHARMACEUTICAL COMPOSITIONS COMPRISING SAME FOR THE TREATMENT OF CARDIOVASCULAR DISORDERS

The present invention relates to digitoxigenin and dihydrodigitoxigenin 3β-derivatives, a process for their preparation and pharmaceutical compositions containing same for the treatment of cardiovascular disorders such as heart failure and hypertension.

The compounds of the present invention have formula (I)

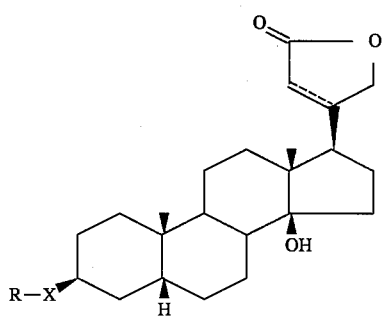

wherein:

the symbol $=$ represents a single or a double bond;
X is S or O;
R is C2–C6 alkyl or C3–C6 alkenyl or alkynyl, unsubstituted or substituted independently by an oxirane group or a quaternary ammonium group or a 2-(2-imidazolinyl) group or one or more Hal, OR1, NR2R3, C(NH)NR4R5;

wherein:
R1 is H or C2–C4 alkyl unsubstituted or substituted by one or more OH or NR6R7; with the proviso that when X is oxygen and R1 is H, R instead of being C2–C6, is C3–C6 and at least another group chosen from NR2R3 or C(NH)NR4R5 is also present in the R group;

R2, R3 are independently H, methyl or C2–C6 alkyl unsubstituted or substituted by NR6R7 or C3–C6 alkenyl or R2 and R3 taken together with the nitrogen atom form an unsubstituted or substituted saturated or unsaturated heteromonocyclic ring optionally containing another heteroatom chosen from oxygen or sulfur or nitrogen, or R2 is hydrogen and R3 is C(NH)NH2;

R4, R5 are independently H, C1–C4 alkyl or C3–C4 alkenyl or R4 and R5 taken together with the nitrogen atom form a penta- or hexa-monoheterocyclic ring;

R6, R7 are independently H, C1–C4 alkyl, or R4 and R5 taken together with the nitrogen atom form a saturated or unsaturated penta- or hexa-monoheterocyclic ring optionally containing another heteroatom chosen from oxygen or sulfur or nitrogen.

The invention includes within its scope all the possible stereoisomers, in particular E and Z isomers, optical isomers and their mixtures and the metabolites and the metabolic precursors of the compounds of formula (I). In particular, when $=$ represents a single bond, both the 20(S) and 20(R) isomers are encompassed within the scope of the present invention.

Pharmaceutical acceptable salts of (I) are salts which retain the biologically activity of the base and are derived from such known pharmacologically acceptable acids such as e.g. hydrochloric, sulfuric, phosphoric, malic, tartaric, maleic, citric, methanesulfonic or benzoic acid.

The alkyl, alkenyl and alkynyl groups may be branched or straight chain groups.

The C2–C6 alkyl group is preferably a C2–C4 alkyl group, e.g. ethyl, propyl, isopropyl, butyl, sec-butyl.

The C3–C6 alkenyl group is preferably a C3–C4 alkenyl group.

The C3–C6 alkynyl group is preferably a C3–C4 alkynyl group.

The quaternary ammonium group is preferably a trimethylammonium- or a N-methylpyrrolidinium- or a N-methylpiperidinium-group.

The Hal group is preferably fluorine, chlorine or bromine.

The OR1 group is preferably hydroxy, 2-aminoethoxy, 3-aminopropoxy, 2-dimethylaminoethoxy, 3-dimethylaminopropoxy, 3-amino-2-hydroxypropoxy, 2,3-diaminopropoxy, 2-(1-pyrrolidinyl)ethoxy, 3-(1-pyrrolidinyl)propoxy.

The NR2R3 group is preferably amino, methylamino, ethylamino, propylamino, isopropylamino, allylamino, propargylamino, dimethylamino, pyrrolidinyl, morpholino, piperazinyl, imidazolyl, guanidino, 2-aminoethylamino, 3-aminopropylamino, 2-(1-pyrrolidinyl)ethylamino, 3-(1-pyrrolidinyl)propylamino, 3-amino-2-hydroxypropylamino, 3-(1-pyrrolidinyl)2-hydroxypropylamino, 2,3-diaminopropylamino.

The C(NH)NR4R5 group is preferably an amidino group.

The NR6R7 is preferably amino, methylamino, ethylamino, propylamino, dimethylamino, pyrrolidinyl, morpholino, piperazinyl, imidazolyl or guanidino.

Preferred examples of specific compounds according to the present invention are:
3β-(2-(trimethylammonium)ethoxy)-14β-hydroxy-5β-card-20(22)-enolide chloride
3β-(2-Aminoethoxy)-14β-hydroxy-5β-card-20(22)-enolide
3β-(3-Aminopropoxy)-14β-hydroxy-5β-card-20(22)-enolide
3β-(2-(1-Pyrrolidinyl)ethoxy)-14β-hydroxy-5β-card-20(22)-enolide
3β-(2-(1-Pyrrolidinyl)propoxy)-14β-hydroxy-5β-card-20(22)-enolide
3β-(3-Dimethylaminopropoxy)-14β-hydroxy-5β-card-20(22)-enolide
3β-(3-(1-Pyrrolidinyl)propoxy)-14β-hydroxy-5β-card-20(22)-enolide
3β-(2-(1-Piperazinyl)ethoxy)-14β-hydroxy-5β-card-20(22)-enolide
3β-(3-(1-Piperazinyl)propoxy)-14β-hydroxy-5β-card-20(22)-enolide
3β-(2-(2-Imidazolin-2-yl)ethoxy)-14β-hydroxy-5β-card-20(22)-enolide
3β-(2-(1-Imidazolyl)ethoxy)-14β-hydroxy-5β-card-20(22)-enolide
3β-(2-Guanidinoethoxy)-14β-hydroxy-5β-card-20(22)-enolide
3β-(3-Amino-2-hydroxypropoxy)-14β-hydroxy-5β-card-20(22)-enolide
3β-(3-(1-Pyrrolidinyl)-2-hydroxypropoxy)-14β-hydroxy-5β-card-20(22)-enolide
3β-(3-(3-Amino-2-hydroxypropoxy)propoxy)-14β-hydroxy-5β-card-20(22)-enolide
3β-(3-(3-Amino-2-hydroxypropylamino)propoxy)-14β-hydroxy-5β-card-20(22)-enolide
3β-(2-(2-dimethylaminoethoxy)ethoxy)-14β-hydroxy-5β-card-(20(22)-enolide 3β-(2-Amidinoethoxy)-14β-hydroxy-5β-card-20(22)-enolide 3β-(2-Hydroxyethylthio)-14β-hydroxy-5β-card-20(22)-enolide 3β-(3-Hydroxypropylthio)-14β-hydroxy-5β-card-20(22)-enolide 3β-(2,3-Epoxypropylthio)-14β-hydroxy-5β-card-20(22)-enolide 3β-(3-Chloro-2-hydroxypropylthio)-14β-hydroxy-5β-card-(20(22)-enolide 3β-(2-(N-Methyl-N-pyrrolidinium)ethylthio)-14β-hydroxy-5β-card-20(22)-enolide chloride 3β-(2-(Trimethylammonium)ethylthio)-14β-hydroxy-5β-card-20(22)-enolide chloride 3β-(2-Aminoethylthio)-14β-hydroxy-5β-card-20(22)-enolide 3β-(3-Aminopropylthio)-14β-hydroxy-5β-card-20(22)-enolide 3β-(4-Amino-(E)-2-butenylthio)-14β-hydroxy-5β-card-20(22)-enolide 3β-(4-Amino-2-butynylthio)-14β-hydroxy-5β-card-20(22)-enolide 3β-(2-Methylaminoethylthio)-14β-hydroxy-5β-card-20(22)-enolide 3β-(2-Dimethylaminoethylthio)-14β-hydroxy-5β-card-20(22)-enolide 3β-(2-(1-Pyrrolidinyl)ethylthio)-14β-hydroxy-5β-card-20(22)-enolide 3β-(3-(1-Pyrrolidinyl)propylthio)-14β-hydroxy-5β-card-20(22)-enolide 3β-(2-(Morpholinoethylthio)-14β-hydroxy-5β-card-20(22)-enolide 3β-(2-(1-Piperazinyl)ethylthio)-14β-hydroxy-5β-card-20(22)-enolide 3β-(3-(1-Piperazinyl)propylthio)-14β-hydroxy-5β-card-20(22)-enolide 3β-(2-(2-Imidazolin-2-yl)ethylthio)-14β-hydroxy-5β-card-20(22)-enolide 3β-(2-(1-Imidazolyl)ethylthio)-14β-hydroxy-5β-card-20(22)-enolide 3β-(2-(2-Amidino)ethylthio)-14β-hydroxy-5β-card-20(22)-enolide 3β-(2-Guanidinoethylthio)-14β-hydroxy-5β-card-20(22)-enolide 3β-(2,3-Dihydroxypropylthio)-14β-hydroxy-5β-card-20(22)-enolide 3β-(3-Amino-2-hydroxypropylthio)-14β-hydroxy-5β-card-20(22)-enolide 3β-(2,3-Diaminopropylthio)-14β-hydroxy-5β-card-20(22)-enolide 3β-(3-(1-Pyrrolidinyl)-2-hydroxypropylthio)-14β-hydroxy-5β-card-20(22)-enolide 3β-(3-(1-Piperazinyl)-2-hydroxypropylthio)-14β-hydroxy-5β-card-20(22)-enolide 3β-(3-(1-Imidazolyl)-2-hydroxypropylthio)-14β-hydroxy-5β-card-20(22)-enolide 3β-(3-Guanidino-2-hydroxypropylthio)-14β-hydroxy-5β-card-20(22)-enolide 3β-(3-(3-Amino-2-hydroxypropoxy)propylthio)-14β-hydroxy-5β-card-20(22)-enolide 3β-(3-(3-Amino-2-hydroxypropylamino)propylthio)-14β-hydroxy-5β-card-20(22)-enolide and the corresponding 3β-thioderivatives 14β-hydroxy-5β-20(S) and 14β-hydroxy-5β-20(R)-cardanolides.

The invention furthermore provides a process for the preparation of said compounds (I), which comprises the condensation of compounds having formula (II)

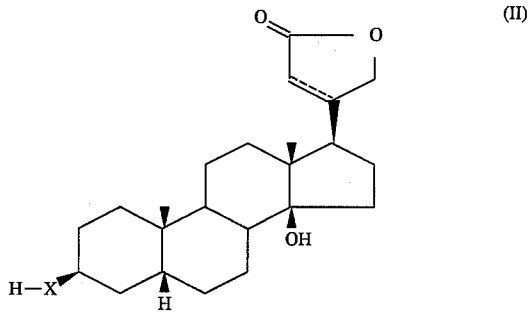

with a compound of formula (III)

R—Y (III)

where Y is an electron-withdrawing group, such as halogen, mesyloxy, or tosyloxy group, which confers electrophilic properties to the attached carbon atom, and R is as above defined. If desired, during the process, the free hydroxy and amino groups optionally present in R are protected with methods well known to those skilled in the art to give, if necessary after removal of protective groups possibly present in R, a compound of general formula (I). The compounds thus obtained may be further converted into another compound of formula (I) or if needed, into a pharmaceutically acceptable salt thereof. If the compound is obtained as a mixture of isomers, the mixture can be resolved via known methods.

The condensation reaction between (II) and (III) is best carried out in an inert aprotic solvent, such as tetrahydrofuran, dioxane, dimethylformamide, dimethylsulfoxyde or in neat (III) and in the presence of a strong base, e.g. sodium or potassium hydride at a temperature ranging from −20° C. to about 110° C. and best with the base added last in small portions.

Due to the presence of a lactone function, care has to be taken to avoid a basic pH during the work-up.

The purification is best performed by flash-chromatography on silica gel.

The invention provides also a process for the preparation of (II), where X is S. Normally the thiols are obtained by reduction of acylthio derivatives with lithium aluminum hydride (Bobbio P. A., *J. Org. Chem.*, 1961, 26, 3023). This method cannot be used in the istant case due to the presence of a reducible lacton function. It has been found, and is part of the present invention, that the free thiols can be obtained by ammonolysis of the acetylthio derivatives (IV), as described in the Prep. 4.

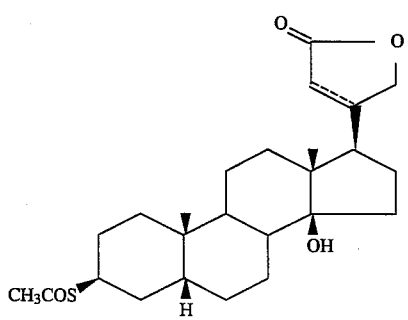

(IV)

The acetylthio derivative (IV-a) wherin an unsaturated lactone is present is a known compound (Abramson H. N. et al., *J. Pharm. Sciences*, 1977, 66, 602) while those with a saturated lactone (IV-b 20(S), see Prep. 5 and IV-c 20(R), see Prep. 6) are new compounds and are obtained by reaction of the 3α-alcohols (V) with thiolacetic acid in the presence of a dialkyl azodicarboxylate and triphenylphosphine.

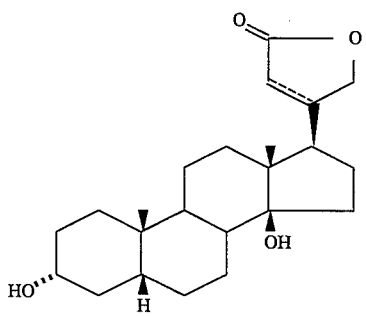

(V)

The 3α-alcohol (V-a) where an unsaturated lactone is present is a known compound (Weiss E,. et al, *Helvetica Chim. Acta*, 1972, 55, 2452) while those with a saturated lactone (V-b (S) and V-c (R)) are new compounds and are obtained by reduction of the corresponding ketones (VI) with a complex hydride.

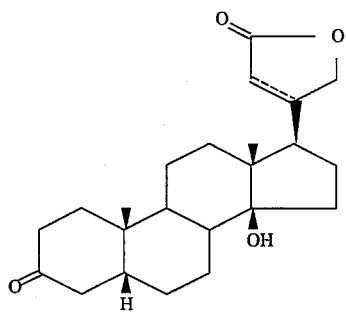

(VI)

The intermediate ketones (VI) are known compounds (Weiss E,. et al, *Helvetica Chim. Acta*, 1972, 55, 2452; Roeder E. and Luetz J., *Arch. Pharm.*, 1985, 318, 837).

The compound of formula (II) where an unsaturated lactone is present and where X is O, is the known compound digitoxygenin (DIGI) (Stoll A. et al, *Helv. Chim. Acta*, 1934, 17, 592).

The compounds of general formula (III) are known compounds, generally commercially available or preparable from known compounds by known methods.

The 3β-derivatives (I) prepared according to the invention and their pharmaceutically acceptable salts have much reduced toxicity compared to aglycones, digitoxigenin (DIGI), dihydrodigitoxigenin 20(S) (DIGI 20(S)) and dihydrodigitoxigenin 20(R) (DIGI 20(R)) and are useful agents for the treatment of cardiovascular disorders such as heart failure and hypertension. Moreover said compounds (I) show high affinity for the receptor site of the $Na^+,K^+$-ATPase and behave as partial agonists on the enzymatic activity of the $Na^+,K^+$-ATPase.

To test the affinity for the receptor site of the $Na^+,K^+$-ATPase and the agonist or inhibitory activity on the enzyme, the following tests were used: a) displacement of the specific $^3$H-ouabain binding from the $Na^+,K^+$-ATPase receptor purified according to Jorghensen (Jorghensen P., *BBA*, 1974,356, 36) and Erdmann (Erdmann E. et al., *Arzneim. Forsh.*, 1984, 34 (II), 1314); b) inhibition of the activity of the purified $Na^+,K^+$-ATPase measured as % of hydrolysis of $^{32}$P-ATP in presence and in absence of the tested compound (Mall F. et al., *Biochem. Pharmacol.*, 1984, 33, 47).

The ability of these compounds to lower blood pressure in adult hypertensive MHS rats was tested by the following method:

systolic blood pressure (SBP) and heart rate (HR) were measured by an indirect tail-cuff method in three-month old hypertensive MHS rats before beginning treatment (basal values). The rats were then subdivided in two groups of 7 animals each, one receiving the compound and the other, the control group, receiving only the vehicle. The compound, suspended in METHOCEL® 0.5% (w/v), for ten days, was administered daily by mouth. SBP and HR were measured daily 6 and 24 hours after the treatment. When ten-day treatment washout had been under way for at least two days, whether the treatment mantains SBP low or re-establish the basal values was verified.

The affinity and the inhibitory activity of the aglycone digitoxigenin (DIGI), dihydrodigitoxigenin 20(S) (DIGI 20(S)) and dihydrodigitoxigenin 20(R) (DIGI 20(R)) and some basic 3β-derivatives on the two tests are shown in the following table:

| Compound | Binding $^3$H-Ouab. Displacement -log IC$_{50}$ | Inhibitory Activity -log IC$_{50}$ |
| --- | --- | --- |
| DIGI | 6.5 | 6.5 |
| DIGI 20(S) | 5.8 | 5.6 |
| DIGI 20(R) | 5.6 | 5.1 |
| Comp. I-a | 7.2 | 6.6 |
| Comp. I-b | 6.7 | 5.3 |
| Comp. I-c | 6.6 | 6.3 |
| Comp. I-d | 6.9 | 6.2 |
| Comp. I-e | 7.0 | 6.0 |
| Comp. I-f | 6.8 | 5.8 |
| Comp. I-h | 7.2 | 6.2 |
| Comp. I-i | 7.0 | 6.2 |
| Comp. I-j | 6.5 | 5.5 |
| Comp. I-k | 7.1 | 6.3 |
| Comp. I-l | 6.6 | 5.7 |
| Comp. I-m | 6.4 | 5.6 |
| Comp. I-n | 6.7 | 6.4 |
| Comp. I-p | 7.0 | 6.1 |
| Comp. I-q | 6.8 | 6.6 |
| Comp. I-r | 6.5 | 6.2 |
| Comp. I-s | 7.1 | 6.2 |
| Comp. I-u | 7.3 | 6.6 |

The activity of the aglycone digitoxigenin (DIGI) and some basic 3β-derivatives in preventing the development of hypertension is shown in the following table:

| SYSTOLIC BLOOD PRESSURE FALL IN SPONTANEOUS HYPERTENSIVE RATS (MHS) | | | | |
| --- | --- | --- | --- | --- |
| Compound | RATS | DOSE* mg/Kg/os | SBP mm Hg | HR beats/min. |
| Controls | 7 | Methocel | 171 +/− 4.5 | 384 +/− 11.0 |
| DIGI | 7 | 20 | 173 +/− 4.0 | 380 +/− 10.0 |
| Comp. I-c | 7 | 20 | 152 +/− 5.0 | 375 +/− 9.0 |
| Comp. I-d | 7 | 20 | 148 +/− 3.2 | 388 +/− 12.0 |
| Comp. I-e | 7 | 20 | 149 +/− 4.8 | 395 +/− 10.0 |
| Comp. I-f | 7 | 20 | 153 +/− 5.1 | 378 +/− 8.5 |
| Comp. I-h | 7 | 20 | 157 +/− 6.0 | 382 +/− 6.8 |
| Comp. I-k | 7 | 20 | 155 +/− 4.2 | 385 +/− 11.0 |
| Comp. I-l | 7 | 20 | 147 +/− 4.8 | 390 +/− 10.0 |
| Comp. I-p | 7 | 20 | 150 +/− 3.5 | 378 +/− 9.3 |
| Comp. I-s | 7 | 20 | 149 +/− 4.1 | 394 +/− 6.3 |
| Comp. I-u | 7 | 20 | 152 +/− 5.2 | 377 +/− 9.0 |

*in Methocel 0.5% w/v

The following examples illustrate the invention without limiting it.

EXAMPLE 1

3β-(2-(1-Pyrrolidinyl)ethoxy)-14β-hydroxy-5β-card-20(22)-enolide (I-a)

To a mixture of 0.50 g of digitoxigenin (DIGI) and 2.0 g of 1-(2-chloroethyl)-pyrrolidine, 0.53 g of potassium hydride (washed with anhydrous ethyl ether and dried under nitrogen) were cautiously added at 90° C. and the resulting suspension was kept at this temperature for 2 hrs.

The reaction mixture was diluted with 10 ml of methylene chloride and glacial acetic acid was added to neutral pH; the organic solvent was washed with water, dried over anhydrous sodium sulfate and evaporated to dryness under reduced pressure.

The residue was purified by column chromatography ($SiO_2$/basic $Al_2O_3$ 1/1) using methylene chloride/methanol 95/5 to 90/10 as eluant, to give 0.33 g of the title compound (I-a) as a pale yellow solid; mp 187°–189° C.

TLC: Rf=0.40 ($SiO_2$ plates, methylene chloride/methanol/30% ammonia solution 90/10/1).

$^1$H-NMR (300 MHz, $CDCl_3$, ppm from TMS): 0.89 (3H, s); 0.94 (3H, s); 2.60 (4H, m); 2.71 (2H, t); 2.80 (1H, dd); 3.53 (2H, m); 3.62 (1H, m); 4.81 (1H, dd); 5.00 (1H, dd); 5.87 (1H, bs).

EXAMPLE 2

3β-(3-Dimethylaminopropoxy)-14β-hydroxy-5β-card-20(22)-enolide (I-b)

Digitoxigenin (DIGI) (0.50 g) was reacted with 3-dimethylamino-1-propyl chloride as described in Ex. 1 to give 0.28 g of the title compound (I-b) as an amorphous solid.

TLC: Rf=0.42 ($SiO_2$ plates, methylene chloride/methanol/30% ammonia solution 90/10/1).

$^1$H-NMR (300 MHz, $CDCl_3$, ppm from TMS): 0.89 (3H, s); 0.94 (3H, s); 2.25 (6H, s); 2.35 (2H, t); 2.80 (1H, dd); 3.52 (2H, t); 3.62 (1H, m); 4.81 (1H, dd); 5.00 (1H, dd); 5.87 (1H, bs).

EXAMPLE 3

3β-(2-(trimethylammonium)ethoxy)-14β-hydroxy-5β-card-20(22)-enolide chloride (I-c)

0.50 g of digitoxigenin (DIGI) was reacted with (2-chloroethyl)trimethylammonium chloride as described in Ex. 1 to give 0.25 g of the title compound (I-c) as an amorphous solid.

TLC: Rf=0.36 ($SiO_2$ plates, methylene chloride/methanol/30% ammonia solution 90/10/1).

$^1$H-NMR (300 MHz, $CDCl_3$, ppm from TMS): 0.89 (3H, s); 0.94 (3H, s); 2.40–2.60 (2H, m); 3.20 (9H, m); 3.70–3.80 (2H, m); 4.15 (1H, bs); 4.81 (1H, dd); 5.00 (1H, dd); 5.87 (1H, bs).

EXAMPLE 4

3β-(3-Aminopropoxy)-14β-hydroxy-5β-card-20(22)-enolide oxalate (I-d)

0.50 g of digitoxigenin (DIGI) was reacted with 3-chloropropylamine hydrochloride as described in Ex.1; the pure compound (0.25 g) obtained by flash-chromatography was dissolved in 2 ml of diethyl ether and a solution of 0.050 g of oxalic acid in 1 ml of diethyl ether was added to give 0.20 g of the title compound (I-d) as a white solid.

TLC: Rf=0.35 ($SiO_2$ plates, methylene chloride/methanol/30% ammonia solution 85/15/1).

$^1$H-NMR (300 MHz, $CDCl_3$, ppm from TMS): 0.78 (3H, s); 0.88 (3H, s); 2.30–2.50 (2H, m); 3.65–3.80 (2H, m); 4.15 (1H, bs); 4.80 (1H, dd); 4.97 (1H, dd); 5.90 (1H, bs).

EXAMPLE 5

3β-(2-(2-dimethylaminoethoxy)ethoxy)-14β-hydroxy-5β-card-20(22)-enolide (I-e)

0.50 g of digitoxigenin (DIGI) was reacted with with 2-bromoethanol as described in Ex.1 to give 0.32 g of 3β-(2-hydroxyethoxy)-14β-hydroxy-5β-card-20 (22)-enolide as a white solid.

TLC: Rf=0.35 ($SiO_2$ plates, n-hexane/ethyl acetate 30/70).

$^1$H-NMR (300 MHz, $CDCl_3$, ppm from TMS): 0.89 (3H, s); 0.99 (3H, s); 3.60–3.80 (4H, m); 4.15 (1H, bs); 4.82 (1H, dd); 5.01 (1H, dd); 5.90 (1 H, dd).

To a solution of 0.90 g of 3β-(2-hydroxyethoxy)-14β-hydroxy-5β-card-20(22)-enolide, in 9 ml of dry pyridine, 0.64 g of tosyl-chloride were added. After 5 hrs 10 ml of water and 50 ml of ethyl acetate were added. The organic phase was washed with water, dried over anhydrous sodium sulfate to give 1.0 g of 3β-(2-tosyloxyethoxy)-14β-hydroxy-5β-card-20(22)-enolide as a colourless oil.

TLC: Rf=0.45 ($SiO_2$ plates, n-hexane/ethyl acetate 80/20).

$^1$H-NMR (300 MHz, $CDCl_3$, ppm from TMS): 0.80 (3H, s); 0.90 (3H, s); 2.45 (3H, s); 3.65–3.80 (2H, m); 4.15–4.25 (3H, m); 4.82 (1H, dd); 5.01 (1H, dd); 5.90 (1H, dd); 7.34 (2H, d); 7.80 (2H, d).

To a solution of 0.21 g of N,N-dimethylethanolamine in 5 ml of dimethylformamide, 0.076 g of KH (20% dispersion in mineral oil) were added, the mixture was heated at 90° C. for 2 hrs and then 0.35 g of 3β-(2-tosyloxyethoxy)-14β-hydroxy-5β-card-20(22)-enolide in 2 ml of dimethylformamide was added. The mixture was kept at the same temperature for 4 hrs and 5 ml of 10% acetic acid were added. The resulting mixture was extracted with methylene chloride, the organic layer was washed with water to neutral pH, dried over anhydrous sodium sulfate and evaporated to dryness under reduced pressure. The crude product was purified by flash-chromatography (SiO$_2$) using methylene chloride/methanol 95/5 as eluant to give 0.22 g of the title compound (I-e) as a white pasty solid.

TLC: Rf=0.31 (SiO$_2$ plates, methylene chloride/methanol/ammonia solution 30% 85/15/1).

$^1$H-NMR (300 MHz, CDCl$_3$, ppm from TMS): 0.80 (3H, s); 0.90 (3H, s); 2.25 (6H, s); 2.38 (2H, t); 3.52 (2H, t); 3.50–3.70 (4H, m); 4.15 (1H, bs); 4.84 (1H, dd); 5.00 (1H, dd); 5.90 (1H, dd).

EXAMPLE 6

3β-(2-Amidinoethoxy)-14β-hydroxy-5β-card-20(22)-enolide oxalate (I-f)

0.50 g of digitoxigenin (DIGI) was submitted to a cyanoethilation with acrylonitrile to give 0.22 g of 3β-(2-cyanoethoxy)-14β-hydroxy-5β-card-20 (22)-enolide as a pale, yellow oil.

TLC: Rf=0.33 (SiO$_2$ plates, n-hexane/ethyl acetate 30/70).

$^1$H-NMR (300 MHz, CDCl$_3$, ppm from TMS): 0.89 (3H, s); 0.99 (3H, s); 2.20–2.30 (2H, m); 3.40–3.50 (2H, m); 4.15 (1H, bs); 4.82 (1H, dd); 5.01 (1H, dd); 5.90 (1H, dd).

A solution of 0.20 g of 3β-(2-cyanoethoxy)-14β-hydroxy-5β-card-20(22)-enolide in 2 ml of dry toluene was added to 0.39 ml of a 1.25M solution of methyl chloroaluminum amide in toluene at room temperature. This solution was heated under argon at 80° C. for 12 hrs. The reaction mixture was cooled and aluminum complex was decomposed by carefully adding of the solution into a slurry of silica gel (20 g) in chloroform. The mixture was stirred for 5 min and the silica gel was filtered. The pure compound (0.25 g) obtained by flash-chromatography was dissolved in 2 ml of diethyl ether and a solution of 0.050 g of oxalic acid in 1 ml of diethyl ether was added to give 0.19 g of the title compound (I-f) as a white amorphous solid.

TLC: Rf=0.31 (SiO$_2$ plates, methylene chloride/methanol/30% ammonia solution 85/15/1).

$^1$H-NMR (300 MHz, DMSO-d$_6$, ppm from TMS): 0.89 (3H, s); 0.99 (3H, s); 2.45–2.55 (2H, m); 3.40–3.50 (2H, m); 4.15 (1H, bs); 4.82 (1H, dd); 5.01 (1H, dd); 5.90 (1H, dd); 6.30 (2H, bs); 6.60 (2H, bs).

EXAMPLE 7

3β-(2-Hydroxyethylthio)-14β-hydroxy-5β-card-20(22)-enolide (I-g)

To 3β-mercapto-14β-hydroxy-5β-card-20(22)-enolide (II-a, Prep. 1) (1.2 g) in 20 ml of dimethylformamide under nitrogen atmosphere at 0° C., 2-bromoethanol (0.77 ml) and 0.012 g of sodium hydride (60% dispersion in mineral oil) were added and the temperature left to rise to 25° C. After 5 hrs the reaction mixture was treated with 0.5M HCl (0.82 ml) to neutralize the excess base and extracted with methylene chloride. The organic solution was washed with a 5% sodium bicarbonate solution, dried over anhydrous sodium sulfate and evaporated to dryness under reduced pressure. The crude product was purified by flash-cromatography (SiO$_2$) using methylene chloride/methanol/30% ammonia solution 95/5/1 as eluant to obtain 0.92 g of the title compound (I-g) as a white solid, mp 82°–85° C.

TLC: Rf=0.35 (SiO$_2$ plates, n-hexane/ethyl acetate 30/70).

$^1$H-NMR (300 MHz, CDCl$_3$, ppm from TMS): 0.89 (3H, s); 0.99 (3H, s); 2.75 (2H, t); 2.80 (1H, bt); 3.26 (1H, bs); 3.72 (2H, t); 4.82 (1H, dd); 5.01 (1H, dd); 5.90 (1H, dd).

EXAMPLE 8

3β-(2,3-Epoxy)propylthio-14β-hydroxy-5β-card-20(22)-enolide (I-h)

3β-Mercapto-14β-hydroxy-5β-card-20(22)-enolide (II-a, Prep. 1) (0.50 g) was reacted with epichlorohydrin (0.2 ml) in 10 ml of dimethylformamide at −15° C. and in the presence of sodium hydride as described in Ex. 7 to give 0.44 g of the title compound (I-h) as a white solid, mp 150°–152° C.

TLC: Rf=0.39 (SiO$_2$ plates, n-hexane/ethyl acetate 55/45).

$^1$H-NMR (300 MHz, CDCl$_3$, ppm from TMS): 0.89 (3H, s); 0.98 (3H, s); 2.05–2.25 (3H, m); 2.53–2.87 (5H, m); 3.07–3.18 (1H, m); 3.48 (1H, bs); 4.80 (1H, dd); 5.00 (1H, dd); 5.89 (1H, bs).

EXAMPLE 9

3β-(2-Aminoethylthio)-14β-hydroxy-5β-card-20(22)-enolide oxalate (I-i)

To a solution of 3β-mercapto-14β-hydroxy-5β-card-20(22)-enolide (II-a, Prep. 1) (0.12 g) and 2-chloroethylamine hydrochloride (0.11 g) in 2.0 ml of dimethylformamide under nitrogen atmosphere, 0.024 g of sodium hydride (60% dispersion in mineral oil) were added at 0° C., and the temperature left to rise to 25° C. After 5 hrs the reaction mixture was treated with 0.5M HCl (0.82 ml) to neutralize the excess base and extracted with methylene chloride. The organic layer was washed with a 5% sodium bicarbonate solution, dried over anhydrous sodium sulfate and evaporated to dryness under reduced pressure. The crude product was purified by flash-cromatography (SiO$_2$) using methylene chloride/methanol/30% ammonia solution 95/5/1 as eluant; the pure compound was dissolved in 2 ml of diethyl ether and a solution of 0.020 g of oxalic acid in 1 ml of diethyl ether was added to give 0.10 g of the title compound (I-i) as a white solid, mp 130°–133° C.

TLC: Rf=0.35 (SiO$_2$ plates, methylene chloride/methanol/30% ammonia solution 98/2/1).

$^1$H-NMR (300 MHz, CDCl$_3$, ppm from TMS): 0.88 (3H, s); 0.99 (3H, s); 2.77 (2H, t); 3.12 (2H, t); 4.90 (1H, dd); 5.05 (1H, dd); 5.90 (1H, dd).

EXAMPLE 10

3β-(2-Aminoethylthio)-14β-hydroxy-5β-20(S) cardanolide oxalate (I-j)

3β-Mercapto-14β-hydroxy-5β-20(S)-cardanolide (II-b, Prep. 2) (0.20 g) was reacted with 2-chloroethylamine hydrochloride (0.18 g) in the presence of sodium hydride as described in Ex. 9 to give 0.15 g of the title compound (I-j) as a white solid, 184°–186° C.

TLC: Rf=0.38 (SiO$_2$ plates, methylene chloride/methanol/30% ammonia solution 90/10/1).

$^1$H-NMR (300 MHz, DMSO-d$_6$, ppm from TMS): 0.85 (3H, s); 0.88 (3H, s); 2.92 (2H, t); 3.25 (1H, bs); 4.00 (1H, t); 4.29 (1H, t).

EXAMPLE 11

3β-(3-Aminopropylthio)-14β-hydroxy-5β-card-20(22)-enolide oxalate (I-k)

3β-Mercapto-14β-hydroxy-5β-card-20(22)-enolide (II-a, Prep. 1) (0.15 g) was reacted with 3-chloropropylamine hydrochloride (0.23 g) in presence of sodium hydride as described in Ex. 9 to give 0.13 g of the title compound (I-k) as a white solid, mp 167°–170° C.

TLC: Rf=0.35 (SiO$_2$ plates, methylene chloride/methanol/30% ammonia solution 85/15/1).

$^1$H-NMR (300 MHz, CDCl$_3$, ppm from TMS): 0.78 (3H, s); 0.88 (3H, s); 2.72 (1H, bt); 2.85 (2H, t); 3.20 (1H, bs); 4.80 (1H, dd); 4.97 (1H, dd); 5.90 (1H, bs).

EXAMPLE 12

3β-(3-Aminopropylthio)-14β-hydroxy-5β-20(S)-cardanolide oxalate (I-l)

3β-Mercapto-14β-hydroxy-5β-20(S)-cardanolide (II-b, Prep. 2) (0.20 g) was reacted with 3-chloropropylamine hydrochloride (0.20 g) in the presence of sodium hydride as described in Ex. 9 to give 0.12 g of the title compound (I-l) as a white solid, mp 176°–178° C.

TLC: Rf=0.22 (SiO$_2$ plates, methylene chloride/methanol/30% ammonia solution 90/10/1).

$^1$H-NMR (300 MHz, DMSO-d$_6$, ppm from TMS): 0.85 (3H, s); 0.88 (3H, s); 2.74 (1H, dd); 2.83 (2H, t); 3.19 (1H, bs); 4.05 (1H, t); 4.29 (1H, t).

EXAMPLE 13

3β-Aminopropylthio)-14β-hydroxy-5β-20(R)-cardanolide oxalate (I-m)

3β-Mercapto-14β-hydroxy-5β-20(R)-cardanolide (II-c, Prep. 3) was reacted with 3-chloropropylamine hydrochloride in the presence of sodium hydride as described in Ex. 9 to give 0.12 g of the title compound (I-m) as a white amorphous solid.

TLC: Rf=0.22 (SiO$_2$ plates, methylene chloride/methanol/30% ammonia solution 90/10/1).

$^1$H-NMR (300 MHz, DMSO-d$_6$, ppm from TMS): 0.83 (3H, s); 0.88 (3H, s); 2.66 (1H, dd); 2.83 (2H, t); 3.19 (1H, bs); 3.90 (1H, t); 4.51 (1H, t).

EXAMPLE 14

3β-(2-(1-Pyrrolidinyl)ethylthio)-14β-hydroxy-5β-card-20(22)-enolide sesquioxalate (I-n)

a) 3β-Mercapto-14β-hydroxy-5β-card-20(22)-enolide (II-a, Prep. 1) was reacted with 0.08 ml of 1-(2-chloroethyl)pyrrolidine in the presence of sodium hydride as described in Ex. 9 to give 0.11 g of the title compound (I-n) as a white solid, mp 104°–107° C.

b) To a solution of 3β-(2-hydroxyethylthio)-14β-hydroxy-5β-card-20(22)-enolide (I-g) (0.40 g) in 9 ml of dry pyridine, 0.22 ml of mesyl chloride were added dropwise at 0° C. The reaction mixture was stirred for 3 hrs at room temperature and then diluted with ethyl acetate and washed with water. The organic layer was dried over sodium sulfate and evaporated to dryness under reduced pressure to give 0.42 g of the mesyloxy derivative, which was reacted without further purification with 2 ml of pyrrolidine in 2 ml of absolute ethanol. The solution was refluxed under nitrogen atmosphere for 3 hrs, then 5 ml of water were added. The resulting mixture was extracted with methylene chloride, the organic layer was dried over sodium sulfate and evaporated to dryness under reduced pressure. The crude product was purified by flash-chromatography (SiO$_2$) using methylene chloride/methanol/30% ammonia solution 95/5/1 as eluant; the pure compound so obtained was dissolved in 2 ml of diethyl ether and a solution of 0.020 g of oxalic acid in 1 ml of diethyl ether was added to give 0.31 g of the title compound (I-n) as a white solid, mp 104°–107° C.

TLC: Rf=0.42 (SiO$_2$ plates, methylene chloride/methanol/30% ammonia solution 90/10/1).

$^1$H-NMR (300 MHz, CDCl$_3$, ppm from TMS): 0.88 (3H, s); 0.97 (3H, s); 3.20–3.35 (3H, m); 3.80–3.95 (2H, m); 4.80 (1H, dd); 5.00 (1H, dd); 5.88 (1H, bs); 12.40 (1H, bs).

EXAMPLE 15

3β-(2-(N-Methyl-N-pyrrolidinium)ethylthio)-14β-hydroxy-5β-card-20(22)-enolide chloride (I-o)

3β-Mercapto-14β-hydroxy-5β-card-20(22)-enolide (II-a, Prep. 1) was reacted with 0.34 g of 1-(2-chloroethyl)-N-methylpyrrolidinium chloride in 7 ml of hexamethylphosphoramide in the presence of sodium hydride as described in Ex. 9 to give 0.29 g of the title compound (I-o) as a white pasty solid.

TLC: Rf=0.15 (SiO$_2$ plates, methylene chloride/methanol/30% ammonia solution 90/10/1).

$^1$H-NMR (300 MHz, CD$_3$OD, ppm from TMS): 0.89 (3H, s); 0.98 (3H, s); 2.20–2.40 (2H, m); 2.90 (3H, s); 3.10–3.30 (7H, m); 4.82 (1H, dd); 5.00 (1H, dd); 5.91 (1H, bs).

EXAMPLE 16

3β-(2-(Trimethylammonium)ethylthio)-14β-hydroxy-5β-card-20(22)-enolide chloride (I-p)

3β-Mercapto-14β-hydroxy-5β-card-20(22)-enolide (II-a, Prep. 1) (0.20 g) was reacted with (2-chloroethyl)trimethylammonium chloride in presence of sodium hydride as described in Ex. 9 to give 0.18 g of the title compound (I-p) as a white solid, mp 230°–235° C.

TLC: Rf=0.18 (SiO$_2$ plates, H$_2$O/nBuOH/AcOH 50/40/10).

$^1$H-NMR (300 MHz, CD$_3$OD, ppm from TMS): 0.88 (3H, s); 0.98 (3H, s); 2.10–2.40 (3H, m); 2.80–3.00 (3H, m); 3.15 (9H, s); 3.35 (1H, bs); 3.50–3.60 (2H, m); 4.90 (1H, dd); 5.05 (1H, dd); 5.90 (1H, bs).

EXAMPLE 17

3β-(3-(1-Pyrrolidinyl)propylthio)-14β-hydroxy-5β-card-20(22)-enolide oxalate (I-q)

3β-Mercapto-14β-hydroxy-5β-card-20(22)-enolide (II-a, Prep. 1) (0.12 g) was reacted with 1-(3-chloropropyl)pyrrolidine (0.090 g) in presence of sodium hydride as described in Ex. 9 to give 0.1 g of the title compound (I-q) as a white solid, mp 174°–177° C.

TLC: Rf=0.29 (SiO$_2$ plates, methylene chloride/methanol/30% ammonia solution 90/10/1).

$^1$H-NMR (300 MHz, CDCl$_3$, ppm from TMS): 0.88 (3H, s); 0.97 (3H, s); 2.57 (2H, t); 2.81 (1H, bt); 3.15–3.45 (4H, m); 4.80 (1H, dd); 5.00 (1H, dd); 5.88 (1H, bs).

EXAMPLE 18

3β-(3-(1-Piperazinyl)propylthio)-14β-hydroxy-5β-card-20(22)-enolide (I-r)

3β-Mercapto-14β-hydroxy-5β-card-20(22)-enolide (II-a, Prep. 1) (0.15 g) was reacted with 1-(3-chloropropyl)piperazine (0.13 g) in presence of sodium hydride as described in Ex. 9 to give 0.090 mg of the title compound (I-r) as a pale yellow solid, mp 87°–90° C.

TLC: Rf=0.30 (SiO$_2$ plates, methylene chloride/methanol/30% ammonia solution 80/20/1).

$^1$H-NMR (300 MHz, CDCl$_3$, ppm from TMS): 0.88 (3H, s); 0.97 (3H, s); 2.05–2.25 (3H, m); 2.42 (6H, bt); 2.52 (2H, t); 2.80 (1H, bt); 2.90 (4H, t); 3.22 (1H, bs); 4.80 (1H, dd); 5.00 (1H, dd); 5.88 (1H, bs).

EXAMPLE 19

3β-(2,3-Dihydroxypropylthio)-14β-hydroxy-5β-card-20(22)-enolide (I-s)

To a solution of 0.20 g of 3β-(2,3-epoxy)propylthio-14β-hydroxy-5β-card-20(22)-enolide (I-h) in 5 ml of tetrahydrofuran/water 2/1, 0.6 ml of 25% aqueous perchloric acid were added and the reaction mixture was stirred at room temperature for 2 hrs. The solution was made basic with solid sodium bicarbonate, concentrated in vacuum and extracted with methylene chloride; the organic layer was washed with water, dried over anhydrous sodium sulfate and evaporated to dryness under reduced pressure; the crude product was purified by flash-chromatography (SiO$_2$) using n-hexane/ethyl acetate 10/90 as eluant to give 0.19 g of the title compound (I-s) as a white solid.

TLC: Rf=0.29 (SiO$_2$ plates, n-hexane/ethyl acetate 20/80).

$^1$H-NMR (300 MHz, CDCl$_3$, ppm from TMS): 0.89 (3H, s); 0.98 (3H, s); 2.50–3.00 (3H, m); 3.20–3.40 (1H, m); 3.70–3.85 (3H, m); 4.80 (1H, dd); 5.00 (1H, dd); 5.89 (1H, bs).

EXAMPLE 20

3β-(3-(1-Pyrrolidinyl)-2-hydroxypropylthio)-14β-hydroxy-5β-card-20(22)-enolide (I-t)

A solution of 0.25 g of 3β-(2,3-epoxy)propylthio-14β-hydroxy-5β-card-20(22)-enolide (I-h) in 2 ml of pyrrolidine was stirred for 48 hrs at room temperature, the excess base was evaporated and the crude product was dissolved in 1 ml of ethyl acetate. To this solution, 0.053 g of oxalic acid in 2 ml of diethyl ether were added, the precipitate was filtered and washed with diethyl ether to give 0.27 g of the title compound (I-t) as a white amorphous solid.

TLC: Rf=0.25 (SiO$_2$ plates, methylene chloride/methanol/30% ammonia solution 80/20/1).

$^1$H-NMR (300 MHz, CD$_3$OD, ppm from TMS): 0.89 (3H, s); 0.98 (3H, s); 2.40–2.55 (2H, m); 3.10–3.35 (6H, m); 3.50 (1H, bs); 3.70–3.80 (1H, bs); 4.82 (1H, dd); 5.00 (1H, dd); 5.91 (1H, bs).

EXAMPLE 21

3β-(3-Amino-2-hydroxypropylthio)-14β-hydroxy-5β-card-20(22)-enolide (I-u)

A solution of 0.25 g of 3β-(2,3-epoxy)propylthio-14β-hydroxy-5β-card-20(22)-enolide (I-h) in 5 ml of dimethylsulfoxide was reacted with sodium azide (0.18 g) for one hr at 60° C. The mixture was diluted with brine and extracted with ethyl acetate. The organic layer was dried with sodium sulfate, filtered and evaporated to dryness under reduced pressure. The crude product was purified by flash-cromatography (SiO$_2$) using n-hexane/ethyl acetate 50/50 as eluant to afford 0.17 g of 3β-(3-azido-2-hydroxypropylthio)-14β-hydroxy-5β -card-20(22)-enolide as an amorphous solid.

TLC: Rf=0.27 (SiO$_2$ plates, n-hexane/ethyl acetate 50/50).

$^1$H-NMR (300 MHz, CDCl$_3$, ppm from TMS): 0.85 (3H, s); 0.93 (3H, s); 2.50–2.80 (3H, m); 3.22 (1H, bs); 3.30–3.45 (2H, m); 3.80–3.90 (1H, bs); 4.82 (1H, dd); 5.00 (1H, dd); 5.85 (1H, bs).

A solution of 0.15 g of 3β-(3-azido-2-hydroxypropylthio)-14β-hydroxy-5β-card-20 (22)-enolide in 2 ml of ethanol was hydrogenated in the presence of 10% palladium on calcium carbonate for 8 hrs. The mixture was filtered on a celite cake and evaporated to dryness under reduced pressure. The crude product was dissolved in ethyl acetate and washed with a solution of sodium carbonate. Evaporation of the solvent afforded 0.13 g of the title compound (I-u) as a white solid, mp 119°–122° C.

TLC: Rf=0.15 (SiO$_2$ plates, methylene chloride/methanol/30% ammonia solution 90/10/1).

$^1$H-NMR (300 MHz, DMSO-d$_6$, ppm from TMS): 0.78 (3H, s); 0.88 (3H, s); 1.90–2.20 (3H, m); 2.72 (1H, bt); 3.20 (1H, bs); 4.10 (1H, s); 4.86 (1H, dd); 4.95 (1H, dd); 5.90 (1H, bs).

PREPARATION OF INTERMEDIATES

Preparation 1

3β-Mercapto-14β-hydroxy-5β-card-20(22)-enolide (II-a)

To a solution of 8.4 g of 3β-acetylthiodigitoxigenin (IV-a) in 500 ml of methanol/tetrahydrofuran 2/1, gaseous ammonia was bubbled in and kept for 3 hrs at room temperature. The mixture was evaporated to dryness under reduced pressure and purified by flash-chromatography (SiO$_2$) using n-hexane/ethyl acetate 60/40 as eluant to give 5.9 g of the title compound (II-a) as a white solid, mp 217°–220° C.

TLC: Rf=0.48 (SiO$_2$ plates, n-hexane/ethyl acetate 60/40).

$^1$H-NMR (300 MHz, CDCl$_3$, ppm from TMS): 0.88 (3H, s); 1.00 (3H, s); 2.78 (1H, bt); 3.60 (1H, bs); 4.81 (1H, dd); 5.01 (1H, dd); 5.88 (1H, bs).

Preparation 2

3β-Mercapto-14β-hydroxy-5β-20(S)-cardanolide (II-b)

By ammonolysis of 3β-acetylthio-14β-hydroxy-5β-20(S)-cardanolide (IV-b) (4.0 g), as described in Prep. 1, 3.2 g of the title compound (II-b) were obtained as a white solid, mp 214°–215° C.

TLC: Rf=0.32 (SiO$_2$ plates, n-hexane/ethyl acetate 60/40).

$^1$H-NMR (300 MHz, CDCl$_3$, ppm from TMS): 0.98 (3H, s); 0.99 (3H, s); 2.70 (1H, dd); 2.78–2.98 (1H, m); 3.60 (1H, bs); 4.05 (1H, t); 4.42 (1 H, t).

Preparation 3

3β-Mercapto, 14β-hydroxy-5β-20(R)-cardanolide (II-c)

Starting from 3β-acetylthio-14β-hydroxy-5β-20(R)-cardanolide (IV-c) and following the procedure hereabove described, the title compound (II-c) was prepared as a white solid, mp 230°–232° C.

TLC: Rf=0.32 (SiO$_2$ plates, n-hexane/ethyl acetate 60/40).

$^1$H-NMR (300 MHz, CDCl$_3$, ppm from TMS): 0.95 (3H, s); 0.99 (3H, s); 2.60 (1H, dd); 2.78–2.98 (1H, m); 3.60 (1H, bs); 3.90 (1H, t); 4.51 (1H, t).

Preparation 4

3β-Acetylthio-14β-hydroxy-5β-card-20(22)-enolide (IV-a)

To a solution of 14 g of 3α,14β-dihydroxy-5β-card-20(22)-enolide (V-a), 10.8 g of triphenylphosphine and 2.9 ml of thiolacetic acid in 150 ml of hexamethylphosphoramide, 8.1 ml of diisopropyl azodicarboxylate were added at room temperature. After 24 hrs the mixture was evaporated to dryness under reduced pressure and the residue was purified by flash-chromatography (SiO$_2$) using n-hexane/ethyl acetate 7/3 as eluant to give 12 g of the title compound (IV-a) as a white solid: mp 212°–215° C. (Abramson, H. N. et al., *J. Pharm. Sciences*, 1977, 66, 602 gives mp 198°–204° C.).

Preparation 5

3β-Acetylthio-14β-hydroxy-5β-20(S)-cardanolide (IV-b)

A mixture of 6.55 ml of diisopropyl azodicarboxylate and 8.7 g of triphenylphosphine in 75 ml of tetrahydrofuran was stirred at 0° C. for 30', then a solution of 5.0 g of 3α,14β-dihydroxy-5β-20(S)-cardanolide (V-b) and 2.4 ml of thiolacetic acid in 75 ml of tetrahydrofuran was added dropwise and the resulting mixture was stirred for one hr at room temperature. The solvent was evaporated to dryness under reduced pressure and the crude product was purified by flash-chromatography (SiO$_2$) using n-hexane/ethyl acetate 60/40 as eluant to give 4.2 g of the title compound (IV-b) as a white solid, mp 174°–177° C.

TLC: Rf=0.34 (SiO$_2$ plates, n-hexane/ethyl acetate 60/40). $^1$H-NMR (300 MHz, CDCl$_3$, ppm from TMS): 0.95 (3H, s); 0.98 (3H, s); 2.31 (3H, s); 2.70 (1H, dd); 2.78–2.98 (1H, m); 4.05 (1H, t); 4.42 (1H, t).

Preparation 6

3β-Acetylthio-14β-hydroxy-5β-20(R)-cardanolide (IV-c)

was analogously obtained as a white solid starting from 3α,14β-dihydroxy-5β-20(R)-cardanolide (V-c): mp 182°–184° C.

TLC: Rf=0.34 (SiO$_2$ plates, n-hexane/ethyl acetate 60/40).

$^1$H-NMR (300 MHz, CDCl$_3$, ppm from TMS): 0.98 (6H, s); 2.20 (1H, dt); 2.31 (3H, s); 2.39 (1H, dd); 2.59 (1H, dd); 2.82–3.00 (1H, m); 3.89 (1H, t); 4.05 (1H, bs); 4.51 (1H, t).

Preparation 7

3α,14β-Dihydroxy-5β-20(S)-cardanolide (V-b)

To a solution of 9.0 g of 3-oxo-14β-hydroxy-5β-20(S)-cardanolide (VI-b) in 700 ml of dioxane, 13.7 g of lithium tri-tert-butoxyaluminum hydride were added at 5°–10° C. After 30' stirring, 500 ml of 5% acetic acid solution were added and the temperature left to rise to 25° C. The dioxane was distilled under vacuum and the remaining mixture extracted with methylene chloride.

The organic layer was dried over anhydrous sodium sulfate and evaporated to dryness under reduced pressure; the crude product was crystallized from ethyl acetate to give 7.1 g of the title compound (V-b) as a white solid, mp 183°–184° C.

TLC: Rf=0.27 (SiO$_2$ plates, n-hexane/ethyl acetate 65/35).

$^1$H-NMR (300 MHz, CDCl$_3$, ppm from TMS): 0.92 (3H, s); 0.97 (3H, s); 2.19 (1H, dd); 2.70 (1H, dd); 2.78–2.98 (1H, m); 3.58–3.72 (1H, m); 4.05 (1H, t); 4.42 (1H, t).

Preparation 8

3α,14β-dihydroxy-5β-20(R)-cardanolide (V-c)

was analogously obtained as a white solid starting from 3-oxo-14β-hydroxy-5β-20(R)-cardanolide (VI-c): mp 195°–198° C.

TLC: Rf=0.27 (SiO$_2$ plates, n-hexane/ethyl acetate 35/65).

$^1$H-NMR (300 MHz. DMSO-d$_6$, ppm from TMS): 0.82 (3H, s); 0.84 (3H, s); 2.42 (1H, dd); 2.70–2.98 (1H, m); 3.86 (1H, t); 4.40 (1H, t).

We claim:

1. Digitoxigenin and dihydrodigitoxigenin 3β-derivatives having formula (I):

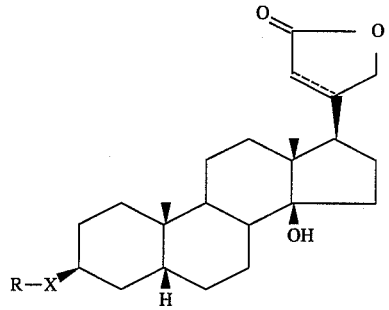

wherein:

the symbol --- represents a single or a double bond;

X is S or O;

R is C2–C6 alkyl or C3–C6 alkenyl, unsubstituted or substituted independently by a quaternary ammonium group or one or more Hal, OR1, NR2R3, C(NH)NR4R5;

wherein:

R1 is H or C2–C4 alkyl unsubstituted or substituted by one or more OH or NR6R7; with the proviso that when X is oxygen and R1 is H, R instead of being C2–C6, is C3–C6 and at least another group chosen from NR2R3 or C(NH)NR4R5 is also present in the R group;

R2, R3 are independently H, methyl or C2–C6 alkyl unsubstituted or substituted by NR6R7 or C3–C6 alkenyl, or R2 is hydrogen and R3 is C(NH)NH2;

R4, R5 are independently H, C1–C4 alkyl or C3–C4 alkenyl;

R6, R7 are independently H, C1–C4 alkyl, and the pharmaceutically acceptable salts thereof.

2. A compound according to claim 1, which is selected from:

3β-(2-(trimethylammonium)ethoxy)-14β-hydroxy-5β-card-(20(22)-enolide chloride
3β-(2-Aminoethoxy)-14β-hydroxy-5β-card-20(22)-enolide
3β-(3-Aminopropoxy)-14β-hydroxy-5β-card-20(22)-enolide
3β-(3-Dimethylaminopropoxy)-14β-hydroxy-5β-card-20(22)-enolide
3β-(2-Guanidino-ethoxy)-14β-hydroxy-5β-card-20(22)-enolide
3β-(3-Amino-2-hydroxypropoxy )-14β-hydroxy-5β-card-20(22)-enolide
3β-(3-(3-Amino-2-hydroxypropoxy)propoxy)-14β-hydroxy-5β-card-20(22)-enolide
3β-(3-(3-Amino-2-hydroxypropylamino)propoxy)-14β-hydroxy-5β-card-20(22)-enolide
3β-(2-(2-dimethylaminoethoxy)ethoxy)-14β-hydroxy-5β-card-20(22)-enolide
3β-(2-Amidinoethoxy)-14β-hydroxy-5β-card-20(22)-enolide
3β-(2-Hydroxyethylthio)-14β-hydroxy-5β-card-20(22)-enolide
3β-(3-Hydroxypropylthio)-14β-hydroxy-5β-card-20(22)-enolide
3β-(3-Chloro-2-hydroxypropylthio)-14β-hydroxy-5β-card-20(22)-enolide
3β-(2-(Trimethylammonium)ethylthio )-14β-hydroxy-5β-card-20(22)-enolide chloride
3β-(2-Aminoethylthio)-14β-hydroxy-5β-card-20(22)-enolide
3β-(3-Aminopropylthio)-14β-hydroxy-5β-card-20(22)-enolide
3β-(4-Amino-(E)-2-butenylthio)-14β-hydroxy-5β-card-20(22)-enolide
3β-(4-Amino-2-butynylthio)-14β-hydroxy-5β-card-20(22)-enolide
3β-(2-Methylaminoethylthio)-14β-hydroxy-5β-card-20(22)-enolide
3β-(2-Dimethylaminoethylthio)-14β-hydroxy-5β-card-20(22)-enolide
3β-(2-(2-Amidino)ethylthio)-14β-hydroxy-5β-card-20(22)-enolide
3β-(2-Guanidinoethylthio)-14β-hydroxy-5β-card-20(22)-enolide
3β-(2,3-Dihydroxypropylthio)-14β-hydroxy-5β-card-20(22)-enolide
3β-(3-Amino-2-hydroxypropylthio)-14β-hydroxy-5β-card-20(22)-enolide
3β-(2,3-Diaminopropylthio)-14β-hydroxy-5β-card-20(22)-enolide
3β-(3-Guanidino-2-hydroxypropylthio)-14β-hydroxy-5β-card-20(22)-enolide
3β-(3-(3-Amino-2-hydroxypropoxy)propylthio)-14β-hydroxy-5β-card-20(22)-enolide
3β-(3-(3-Amino-2-hydroxypropylamino)propylthio)-14β-hydroxy-5β-card-20 (22)-enolide and the corresponding 3β-thioderivatives 14β-hydroxy-5β-20(S) and 14β-hydroxy-5β-20(R)-cardanolides.

3. A pharmaceutical composition comprising a compound of formula (I) or a pharmaceutically acceptable salt thereof and a pharmaceutically acceptable carrier and/or diluent.

4. An orally or parenterally administrable pharmaceutical composition for the treatment of cardiovascular disorders comprising an effective amount of a compound of formula (I) or an equivalent amount of a pharmaceutically acceptable salt thereof and an excipient and/or diluent therefor.

5. The composition of claim 4 for the treatment of hypertension.

6. The composition of claim 4 for the treatment of cardiac failure.

7. Digitoxigenin and dihydrodigitoxigenin 3β-derivatives having the formula (I):

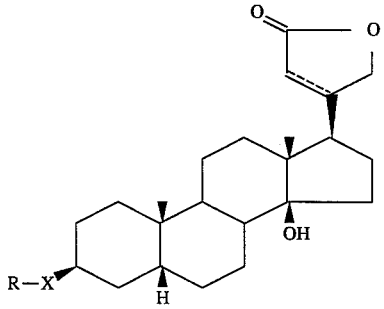

wherein:
the symbol --- represents a single or a double bond;
X is S;
R is C2–C6 alkyl or C3–C6 alkenyl, unsubstituted or substituted independently by a quaternary ammonium group or one or more Hal, OR1, NR2R3, C(NH)NR4R5;

wherein:
R1 is H or C2–C4 alkyl unsubstituted or substituted by one or more OH or NR6R7;

R2, R3 are independently H, methyl or C2–C6 alkyl unsubstituted or substituted by NR6R7 or C3–C6 alkenyl, or R2 is hydrogen and R3 is C(NH)NH2;

R4, R5 are independently H, C1–C4 alkyl or C3–C4 alkenyl;

R6, R7 are independently H, C1–C4 alkyl, and the pharmaceutically acceptable salts thereof.

8. Digitoxigenin and dihydrodigitoxigenin 3β-derivatives having the formula (I):

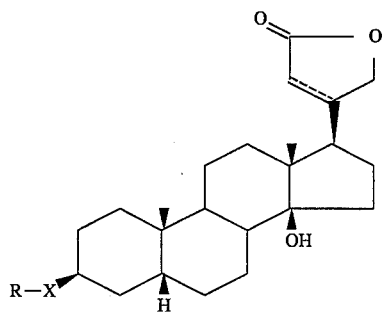

wherein:

the symbol --- represents a single or a double bond;
X is S or O;
R is C3–C6 alkenyl, unsubstituted or substituted independently by a quaternary ammonium group or one or more Hal, OR1, NR2R3, C(NH)NR4R5;
wherein:
R1 is H or C2–C4 alkyl unsubstituted or substituted by one or more OH or NR6R7; with the proviso that when X is oxygen and R1 is H, R instead of being C2–C6, is C3–C6 which is substituted with at least one group chosen from NR2R3 or C(NH)NR4R5;
R2, R3 are independently H, methyl or C2–C6 alkyl unsubstituted or substituted by NR6R7 or C3–C6 alkenyl, or R2 is hydrogen and R3 is C(NH)NH2;
R4, R5 are independently H, C1–C4 alkyl or C3–C4 alkenyl;
R6, R7 are independently H, C1–C4 alkyl, and the pharmaceutically acceptable salts thereof.

9. Digitoxigenin and dihydrodigitoxigenin 3β-derivatives having the formula (I):

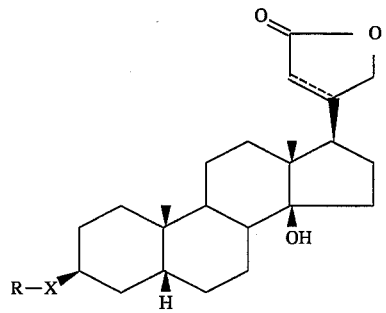

wherein:

the symbol --- represents a single or a double bond;
X is S or O;
R is C2–C6 alkyl substituted independently by a quaternary ammonium group or one or more Hal, OR1, NR2R3, C(NH)NR4R5;
wherein:
R1 is H or C2–C4 alkyl unsubstituted or substituted by one or more OH or NR6R7; with the proviso that when X is oxygen and R1 is H, R instead of being C2–C6, is C3–C6 which is substituted with at least one group chosen from NR2R3 or C(NH)NR4R5;
R2, R3 are independently H, methyl or C2–C6 alkyl unsubstituted or substituted by NR6R7 or C3–C6 alkenyl, or R2 is hydrogen and R3 is C(NH)NH2;
R4, R5 are independently H, C1–C4 alkyl or C3–C4 alkenyl;
R6, R7 are independently H, C1–C4 alkyl, and the pharmaceutically acceptable salts thereof.

* * * * *